(12) United States Patent
Groves

(10) Patent No.: US 8,584,509 B2
(45) Date of Patent: Nov. 19, 2013

(54) ENVIRONMENTAL MONITORING SYSTEM AND METHOD WITH A PREFILTER

(75) Inventor: Bruce D. Groves, Madison, NJ (US)

(73) Assignee: Emilcott Associates, Inc., Chatham, NJ (US)

( * ) Notice: Subject to any disclaimer, the term of this patent is extended or adjusted under 35 U.S.C. 154(b) by 798 days.

(21) Appl. No.: 12/650,951

(22) Filed: Dec. 31, 2009

(65) Prior Publication Data

US 2011/0156715 A1 Jun. 30, 2011

(51) Int. Cl.
*G01N 7/00* (2006.01)
*G01N 33/497* (2006.01)

(52) U.S. Cl.
USPC .......................... 73/31.01; 73/23.2; 436/126

(58) Field of Classification Search
USPC .......... 324/466; 73/31.01, 23.2, 30.03–30.01, 73/31.02; 436/126
See application file for complete search history.

(56) References Cited

U.S. PATENT DOCUMENTS

| | | | |
|---|---|---|---|
| 5,654,498 A | 8/1997 | Kessel | |
| 6,333,632 B1 * | 12/2001 | Yang et al. | 324/464 |
| 7,241,989 B2 | 7/2007 | Miller et al. | |
| 7,302,313 B2 * | 11/2007 | Sharp et al. | 700/276 |
| 7,704,748 B2 * | 4/2010 | Schaeffer et al. | 436/160 |
| 7,777,179 B2 * | 8/2010 | Chen et al. | 250/281 |
| 8,054,082 B2 * | 11/2011 | Brothier et al. | 324/468 |
| 8,205,483 B1 * | 6/2012 | Peterson et al. | 73/38 |
| 8,258,794 B2 * | 9/2012 | Rziha | 324/466 |
| 8,336,402 B2 * | 12/2012 | Glezer et al. | 73/863.81 |
| 8,479,558 B2 * | 7/2013 | Dimmler et al. | 73/23.34 |
| 2002/0048818 A1 * | 4/2002 | Sakairi et al. | 436/126 |
| 2007/0012185 A1 | 1/2007 | Taylor, Jr. et al. | |
| 2008/0148816 A1 * | 6/2008 | Groves | 73/31.01 |
| 2009/0090167 A1 * | 4/2009 | Groves | 73/31.01 |
| 2009/0095054 A1 * | 4/2009 | Groves | 73/31.01 |
| 2009/0113990 A1 * | 5/2009 | Groves | 73/31.01 |

* cited by examiner

Primary Examiner — Joshua Benitez-Rosario
(74) Attorney, Agent, or Firm — Glen M. Diehl

(57) ABSTRACT

Various environmental systems are disclosed. In accordance with one of the systems, a first and second valve are provided. The valves provide a first air flow path from an air pump to a photo-ionization detector is provided through a pre-filter. The valves also provide a second air flow path from the air pump to the photo-ionization detector so that the pre-filter is isolated from its environmental surroundings. Various other arrangements of environmental monitoring systems with one or more pre-filters are also disclosed.

9 Claims, 6 Drawing Sheets

ENVIRONMENTAL MONITORING SYSTEM AND METHOD WITH A PREFILTER

BACKGROUND

Photo-ionization detectors (PIDs), flame-ionization detectors (FIDs) and related volatile gas detection devices are well-established, commercially available product designs capable of measuring the total airborne concentration of volatile organic compounds (VOCs) present in the inlet air of the device. Such devices are offered by a number of manufacturers. For example, RAE Systems offers a range of PIDs, and Photovac and Thermo Fisher each offer both a PID and an FID. Some of these devices rely on the ionization properties of VOCs to create a measureable signal that can be correlated to the concentration of these compounds.

The PID related volatile gas detection devices sample air continuously, using a pump to induce a precisely regulated flow through the device. Hence, the measurement of total VOC concentration can be in real-time and continuously updated. Modern PIDs are typically equipped with a computer interface, including a physical data port and a set of programming instructions. This allows the user to create custom software that operates the PID and acquires VOC measurements and other data from the PID.

As an adjunct to the PID, a pre-filter can be employed to prevent interfering VOCs from entering the inlet airflow of the PID, permitting only a specific VOC, or set of VOCs, of interest to pass into the PID. The pre-filter is placed in the inlet air stream of the PID so that the filtering action occurs prior to the measurement of the air sample. This, in turn will permit the PID's measurement of a VOC to reflect only the concentration of the specific compound of interest. Such pre-filters are commercially available, for example from Draeger or RAE Sytems, and are used to monitor the concentration of benzene or other substances of interest. These pre-filters physically trap other, interfering VOCs that are not to be measured, preventing those compounds from being detected by the PID.

Nevertheless, there are challenges and constraints associated with the proper usage of pre-filters. Such pre-filters typically have a finite service life and will eventually become invalid after prolonged exposure to the atmosphere, due to saturation by VOCs and to effects of temperature and humidity. They are thus perishable items that must be replaced when no longer suitable for service. The duration of the valid service life of a given pre-filter will depend on various factors, such as the specific chemical constituents and their concentrations in the ambient air to which the pre-filter is exposed, the cumulative volume of air that flows through the pre-filter, the duration of exposure of the pre-filter, and the ambient temperature and humidity.

U.S. Pat. No. 5,654,498 discloses a device for the selective detection of a component in a gas mixture, or a pre-filter that is useful in the various aspects of the present invention.

SUMMARY

A photo-ionization detector (PID), flame ionization detector (FID) or other viable volatile gas detector can be used in conjunction with a compound-specific pre-filter to produce a direct measurement of the airborne concentration of the compound of interest, for example Benzene. Since such pre-filters have a finite service life due to contamination and/or saturation, they must be utilized on a limited basis and under controlled conditions. This invention presents techniques for automatically initiating operation of a PID/filter configuration upon the occurrence of a triggering event, for example a threshold level of total volatile organic compound (VOC) concentration or some other process measurement. These techniques will enable real-time measurement of the concentration of a specific compound, for a finite duration dependent on the performance of the pre-filter. Moreover, these techniques can be fully automated via a computer interface to the PID.

In accordance with one aspect of the present invention, a system for monitoring an environment is provided. The system includes a first valve having an inlet that is adapted to receive air from the environment and a first and second outlet, a second valve having a first and second inlet and an outlet, the first inlet being connected to the first outlet of the first valve, a pre-filter connected between the second outlet of the first valve and the first inlet of the second valve, the pre-filter selectively preventing one or more compounds from the environment from passing further through the airflow network, and a detector having an inlet connected to the outlet of the second valve, the detector determining a concentration of one or more volatile organic compounds in real-time. The first valve and the second valve are configured to either allow air flow from the first outlet of the first valve through the second valve to the detector or from the second outlet of the first valve through the pre-filter to the first inlet of the second valve to the detector.

The detector is selected from the group consisting of a photo ionization detector, a flame ionization detector, a spectrophotometer and an electrochemical detector.

The system may include a computerized monitoring system connected to the valves that transmits one or more control signals to the first valve and the second valve to control positions of the first valve and the second valve.

The system may also include a sensor connected to the computerized monitoring system wherein a status of the sensor determines the one or more control signals.

The system may also include an air pump connected to the inlet of the first valve or to the outlet of the PID. In either case, the air pump helps create the proper airflow through the system.

In accordance with another aspect of the invention, the system may also include a second pre-filter having an inlet connected to a third outlet of the first valve and an outlet connected to a third inlet of the second valve, wherein the first valve and the second valve are configured to either allow air flow from the first outlet of the first valve through the second valve to the detector or from the second outlet of the first valve through the pre-filter to the first inlet of the second valve to the detector or from the third outlet of the first valve through the second pre-filter to the third inlet of the second valve to the detector. In accordance with a further aspect of the present invention, they system may also include a third pre-filter having an inlet connected to a fourth outlet of the first valve and an outlet connected to a fourth inlet of the second valve, wherein the first valve and the second valve are configured to either allow air flow from the first outlet of the first valve through the second valve to the detector or from the second outlet of the first valve through the pre-filter to the first inlet of the second valve to the detector or from the third outlet of the first valve through the second pre-filter to the third inlet of the second valve to the detector or from the fourth outlet of the first valve through the third pre-filter to the fourth inlet of the second valve to the detector.

In accordance with a further aspect of the present system, an environmental monitoring system is provided. The system includes a detector having an inlet, the detector determining a concentration of one or more volatile organic compounds. It can also include a first valve connected to the detector which allows air to flow into the detector when open and prevents air from flowing into the detector when closed. The system further includes a first pre-filter having an inlet and an outlet, a second valve connected to the inlet of the first pre-filter and a third valve connected to the outlet of the first pre-filter, the second valve being connected to the detector, wherein air flows through the first pre-filter only when the second valve and the third valve are both open. The system also includes a second pre-filter having an inlet and an outlet, a fourth valve connected to the inlet of the second pre-filter and a fifth valve connected to the outlet of the second pre-filter, the fourth valve being connected to the detector, wherein air flows through the second pre-filter only when the fourth valve and the fifth valve are both open. The first and second pre-filters selectively remove one or more compounds from the environment. As before, the detector can be selected from the group consisting of a photo ionization detector, a flame ionization detector, a spectrophotometer and combinations thereof. Also, an air pump can be provided upstream of the first valve, the second valve and the fourth valve. Alternatively, an air pump can be provided at the outlet of the PID. Operationally, in accordance with an aspect of the invention, only the first valve is open, only the second and third valves are open or only the fourth and fifth valves are open. A computerized monitoring system can be provided to control the first through fifth valves. In accordance with further aspects of the present invention, the system can include a third pre-filter having an inlet and an outlet, a sixth valve connected to the inlet of the third pre-filter and a seventh valve connected to the outlet of the third pre-filter, the seventh valve being connected to the ionization detector, wherein air flows through the third pre-filter only when the sixth valve and the seventh valve are both open.

An environmental monitoring system in accordance with another aspect of the present invention can include a first air pump inducing flow through a first detector. The first detector determines a concentration of one or more volatile organic compounds in real-time. The system also can include a second air pump inducing flow through a system comprised of a first check valve that is connected to a pre-filter that is connected to a second valve that is connected to a second detector. The second detector determines a concentration of one or more volatile organic compounds in real-time. The first detector is co-located with the second detector. The first detector can be is selected from the group consisting of a photo ionization detector, a flame ionization detector, a spectrophotometer and combinations thereof. The second detector can also be selected from the same group.

DESCRIPTION

Figure 1:
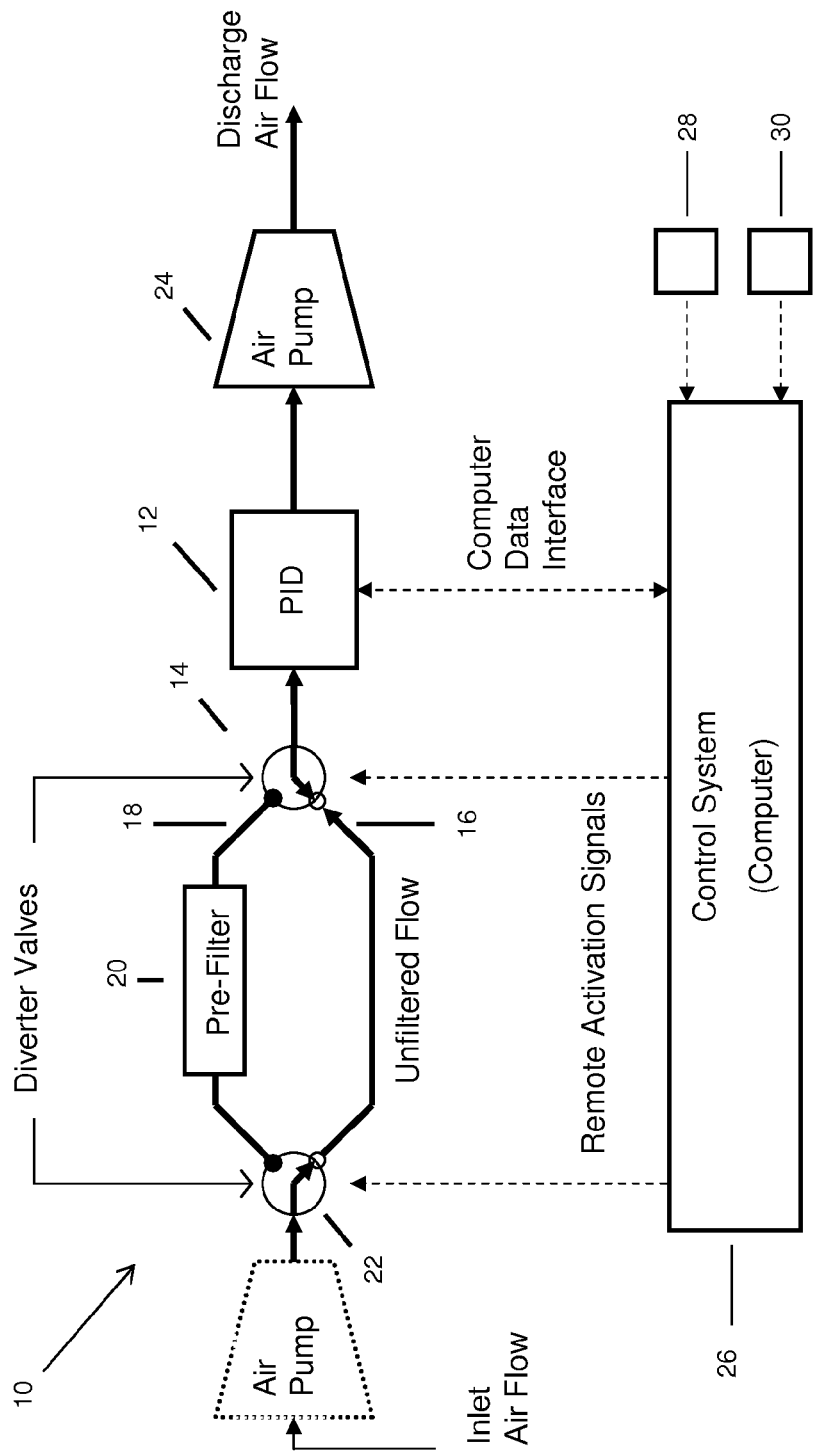
FIG. 1 illustrates a system in accordance with one aspect of the present invention.

FIG. 1 illustrates a system 10 in accordance with one aspect of the present invention. The system uses a single PID 12 with flow diversion. In this configuration, the PID 12 is equipped with a bifurcated inlet manifold 14 in the form of a diverter valve. One branch 16 of the manifold 14 is unobstructed to the inlet of the PID 12, while the other branch 18 is routed through a pre-filter 20, as shown.

Air flow is induced through the system by an air pump 24. In practice, the pump can be positioned on the upstream (inlet) side of the system pushing air through, or on the downstream (discharge) side pulling air through. Depending on the position of the upstream diverter 22, the air flow is either provided directly to the bifurcated inlet manifold 14 or through the pre-filter 20.

The bifurcated inlet manifold 14, the diverter 22 and the pump 24 are readily available off-the-shelf components. For some commercially available PIDs, a pump is provided integral to the chassis of the device. However, for purposes of this writing, the PID represents the VOC measurement device distinct from the pump that is inducing air flow through the system of interest.

In accordance with one aspect of the present invention, initially, this system 10 is in steady-state operation with inlet flow to the PID 12 through the open side of the manifold and the PID 12 continuously monitors total VOC concentration. Thus, the diverter 22 and the bifurcated inlet manifold 14 are both controlled to be in the positions indicated in FIG. 1.

The control signals for the diverter 22 and the bifurcated inlet manifold 14 are preferably provided by a computer system 26. The computer system 26 can be part of an environmental monitoring station, and can include servers and individual client stations connected to the servers that may be located remotely from the system 10. The control of the diverter 22 and the manifold 14 can be effectuated by processors in either the server or the client stations, or even a standalone computer co-located with the system 10.

The computer 26 can send control signals to control the diverter 22 and the manifold 14. These signals can be sent by wire or wirelessly. If sent wirelessly, the diverter 22 and the manifold 14 are equipped with an appropriate modem and/or wireless modem to receive the wireless signals. The control signals cause the diverter 22 and manifold 14 to switch to divert flow from the air pump 24 to the pre-filter 20 through the manifold 14 to the PID 12. Thus, the diverter valves 22 and 14 are actuated so that inlet flow to the PID 12 is exclusively routed through the pre-filter 20. In this configuration, the PID 12 will report only the concentration of the substance of interest for which the pre-filter 20 is configured.

The activation signals can be sent periodically or on the occurrence of a triggering event by an alarm 28 or other sensor 30. One such technique would be to trigger based on a pre-established threshold of total VOC concentration measured by the PID 12 of unfiltered flow through the unobstructed branch 16 of the manifold. The triggering signal may be electrical, mechanical, hydraulic, etc., such that it can actuate the diverter valves. This signal may emanate from a computer software application, another measurement instrument, an alarming device, etc., as suits the needs of the VOC measurement application. This event may be, but is not restricted to, a threshold level of total VOC concentration from the PID in this system. For example, the triggering event may be a threshold level of another environmental parameter, or the occurrence of a specified time of day. The duration for which the PID inlet flow is routed through the pre-filter will also depend on the requirements of the measurement application.

At the conclusion of the measurement using the pre-filter, the inlet to the PID 12 will switch back to the unfiltered flow, either automatically or manually. At the conclusion of the measurement using the pre-filter 20, the inlet flow can be routed through the unfiltered leg 16, either automatically or manually, and the diverter valves 14 and 22 can be adjusted so as to isolate the pre-filter 20. The conclusion of the measurement can be triggered by a computer software application; a pre-determined period of time, e.g., a 15-minute exposure test; another measurement instrument; an alarming device, etc.

This system 10 offers the advantage of using the pre-filter 20 only when needed and keeping the pre-filter 20 isolated when it is not needed. This expands the life of the pre-filter 20 and significantly improves the accuracy and usefulness of the system 10.

Figure 2:
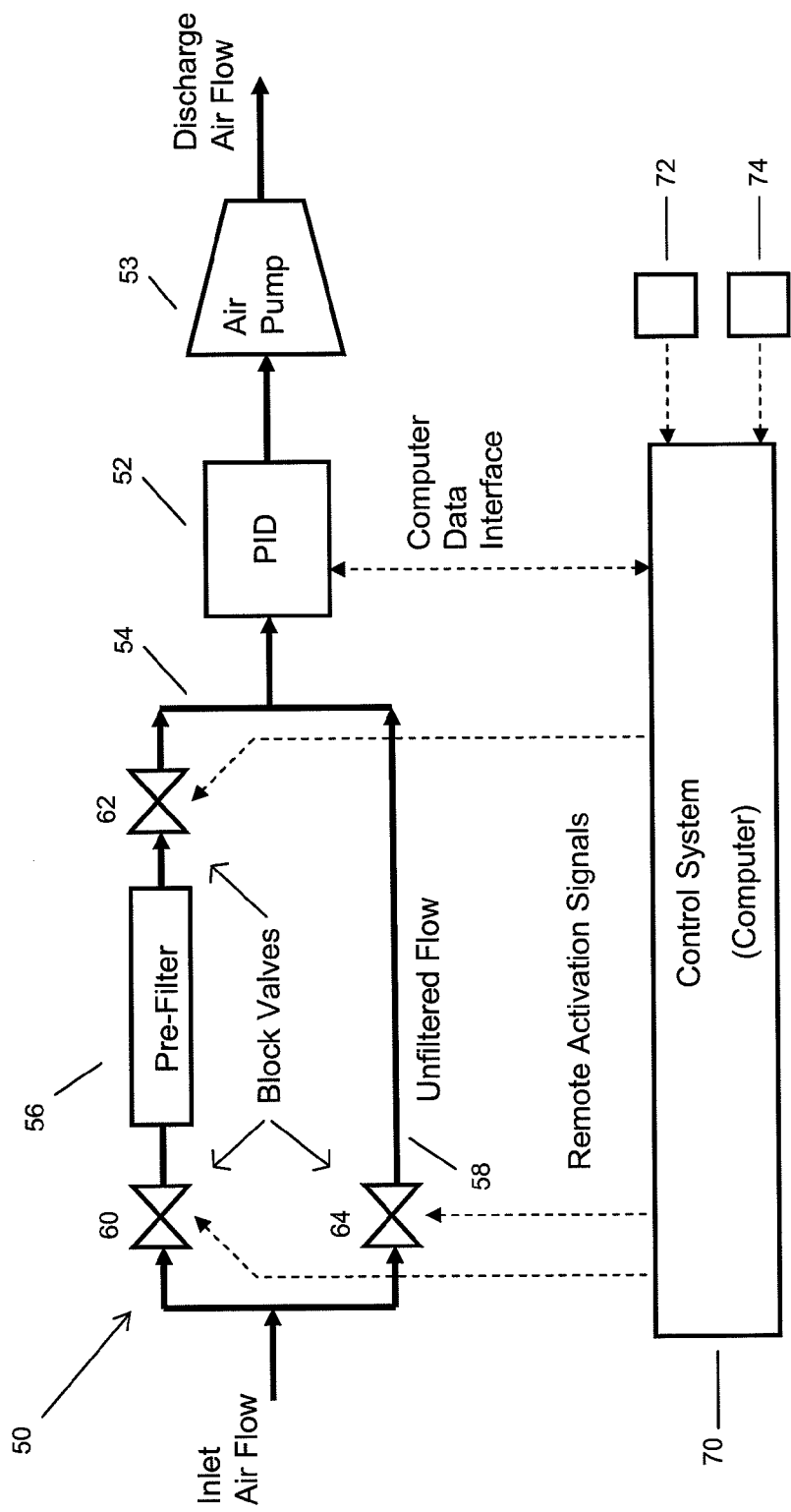
FIG. 2 illustrates a system having block valves and remote activation signals in accordance with another aspect of the present invention.

FIG. 2 illustrates a system 50 having block valves and remote activation signals in accordance with another aspect of the present invention. This system 50 uses block valves instead of diverter valves to regulate the flow of air through the pre-filter. In this configuration, the PID 52 is equipped with a bifurcated inlet manifold 54, with one branch of the manifold controlled by block valves 60 and 62, while the other branch is controlled by block valve 64.

Air flow is induced through the system by an air pump 53. In practice, the pump can be positioned on the upstream (inlet) side of the system pushing air through, or on the downstream (discharge) side pulling air through. Depending on the states of the block valves 60, 62 and 64, the air flow is either provided directly to the unfiltered leg of the manifold 58 or through the pre-filter 56.

Either on a periodic basis or upon occurrence of a triggering event, the control system 70 will cause the block valves 60 and 62 to be opened and the block valve 64 to become closed, thus permitting air flow through the pre-filter 56 and initiating measurement of the concentration of the substance of interest by PID 52.

As before, the triggering signal may be electrical, mechanical, hydraulic, etc., such that it can actuate the block valves 60, 62 and 64. This triggering signal may emanate from a computer software application, another measurement instrument 72, an alarming device 74, etc., as suits the needs of the VOC measurement application. This event may be, but is not restricted to, a threshold level of total VOC concentration from the PID 52 in this system. The duration for which the PID 52 inlet flow is routed through the pre-filter 56 will also depend on the requirements of the measurement application.

At the conclusion of the measurement using the pre-filter 56, the inlet flow can be routed through the unfiltered leg 58, either automatically or manually, by opening block valve 64 and closing the block valves 60 and 62 so as to isolate the pre-filter 56. The conclusion of the measurement can be triggered by a computer software application; a pre-determined period of time, e.g., a 15-minute exposure test; another measurement instrument; an alarming device, etc. This event may be, but is not restricted to, a threshold level of total VOC concentration from the PID 52 in this system.

Figure 3:
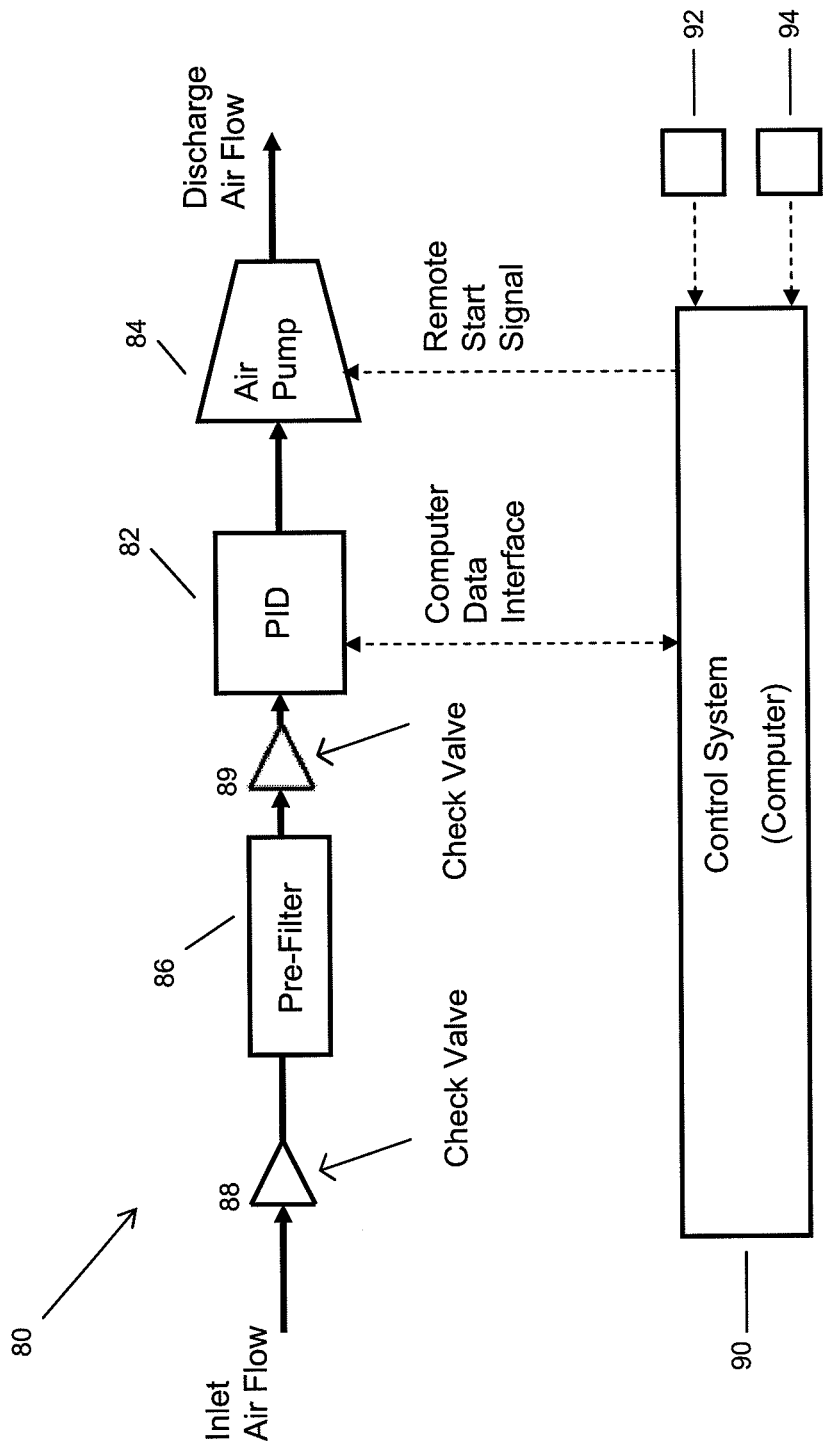
FIG. 3 illustrates a system having a check valve and a remote start signal in accordance with a further aspect of the present invention.

FIG. 3 illustrates a system 80 in accordance with another aspect of the present invention. The system 80 includes an air pump 84 connected directly to PID 82. The inlet to the PID 82 can be connected directly to the outlet of the pre-filter 86, while the inlet side of the pre-filter 86 is connected to a check valve 88 that permits flow only toward the pre-filter. A check valve 89 is illustrated connected between the pre-filter 86 and the PID 82. The check valve 89 is optional in this embodiment of the present invention.

In this system 80, inlet flow to the filtered PID 82 is controlled by starting the air pump 84, which in turn induces a negative air pressure through the PID 82 and pre-filter 86, thus causing the check valve 88 to open and allow inlet air to be drawn through the system. In this configuration, the PID 82 will report only the concentration of the substance of interest for which the pre-filter 86 is configured.

The triggering signal may be electrical, mechanical, hydraulic, etc., such that it can start the air pump 84. This triggering signal may emanate from a computer software application which may be located in the control system 90, another measurement instrument 92, an alarming device 94, etc., as suits the needs of the VOC measurement application.

At the conclusion of the measurement using the pre-filter 88, the inlet flow can be stopped by stopping the air pump, either automatically or manually. The conclusion of the measurement can be triggered by a computer software application; a pre-determined period of time, e.g., a 15-minute exposure test; another measurement instrument; an alarming device, etc.

Figure 4:
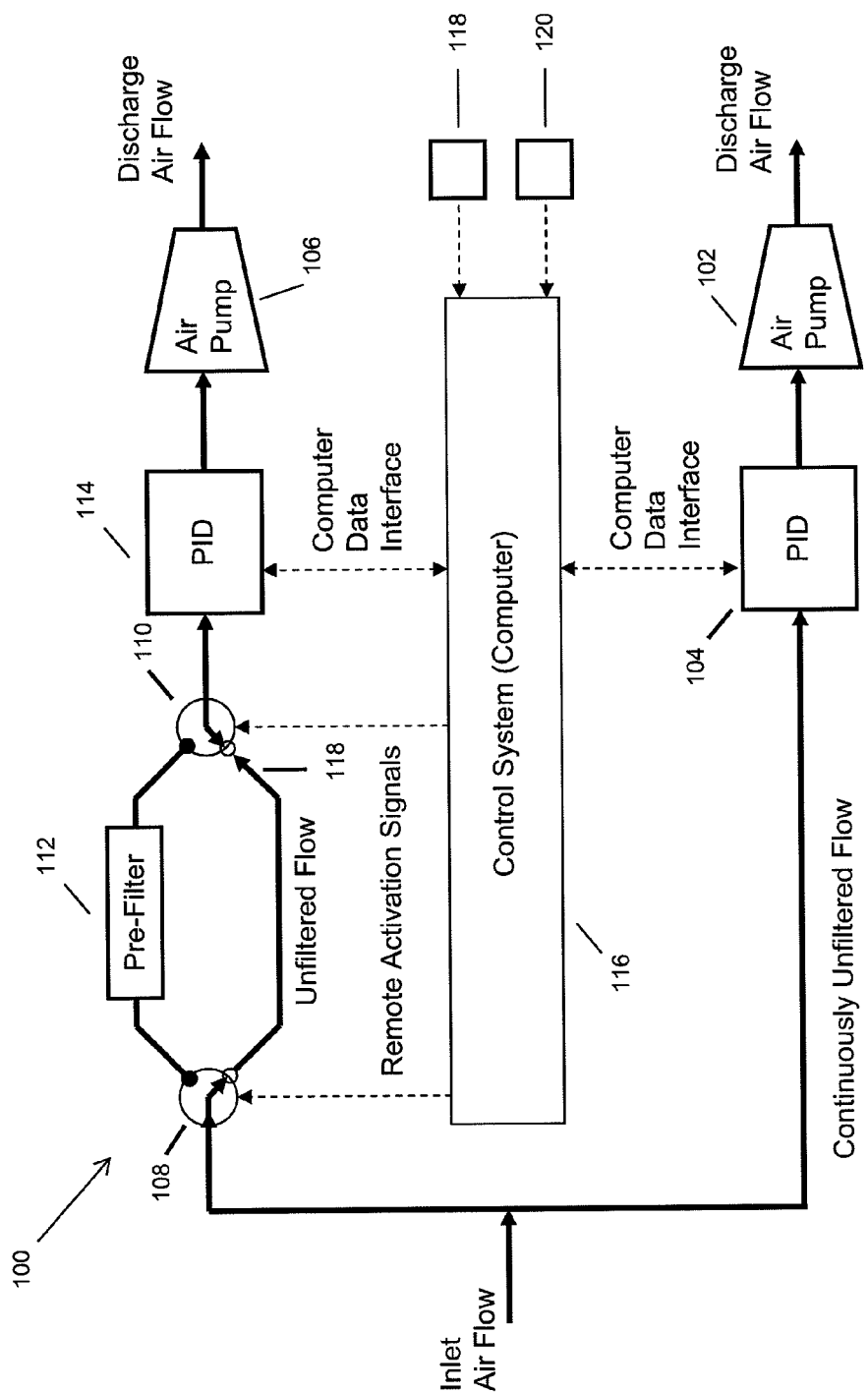
FIG. 4 illustrates a system having diverter valves and remote activation signals and second PID in accordance with one aspect of the present invention.

FIG. 4 illustrates a system 100 in accordance with another aspect of the present invention. The system includes a first air pump 102 and a first PID 104. It also includes a second air pump 106 connected to a first diverter valve 108. One outlet of the first diverter valve 108 is connected to a first inlet of a second diverter valve 110. A second outlet of the first diverter valve 108 is connected an inlet of an appropriately selected pre-filter 112. The outlet of the pre-filter 112 is connected to a second inlet of the second diverter valve 110. The outlet of the second diverter valve 110 is connected to a second PID 114. The second PID 114 is preferably controlled by a computer 116, but it may also be manually controlled. The computer 116 can also control the diverter valves 108 and 110.

The two PID's 104 and 114 are preferably in close proximity to one another, typically adjacent so that their inlet air flow is drawn from the same samples. The second PID 114 can be fully operational prior to being engaged for filtered service. One advantage of this configuration is that, prior to engaging the filter 112, the two PIDs will both measure the same inlet air sample, thus providing a correlation consistency check on the accuracy and precision of their VOC measurements. As an alternative configuration, this system could be operated with a single air pump connected to a discharge manifold common to the outlets of both PIDs.

As before, the triggering signal may be electrical, mechanical, hydraulic, etc., such that it can actuate the diverter valves 108 and 110. This triggering signal may emanate from a computer software application, another measurement instrument, an alarming device, etc., as suits the needs of the VOC measurement application. This event may be, but is not restricted to, a threshold level of total VOC concentration from either PID 104 or PID 114 in this system. The duration for which the PID 114 inlet flow is routed through the pre-filter 112 will also depend on the requirements of the measurement application.

At the conclusion of the measurement using the pre-filter 112, the inlet flow can be routed through the unfiltered leg 118 of the inlet to PID 114, either automatically or manually, so as to isolate the pre-filter 112. The conclusion of the measurement can be triggered by a computer software application; a pre-determined period of time, e.g., a 15-minute exposure test; another measurement instrument; an alarming device, etc. This event may be, but is not restricted to, a threshold level of total VOC concentration from PID 104 in this system. The sensors 118 and 120 can provide the start and stop control signals for each of the devices in FIG. 4.

Figure 5:
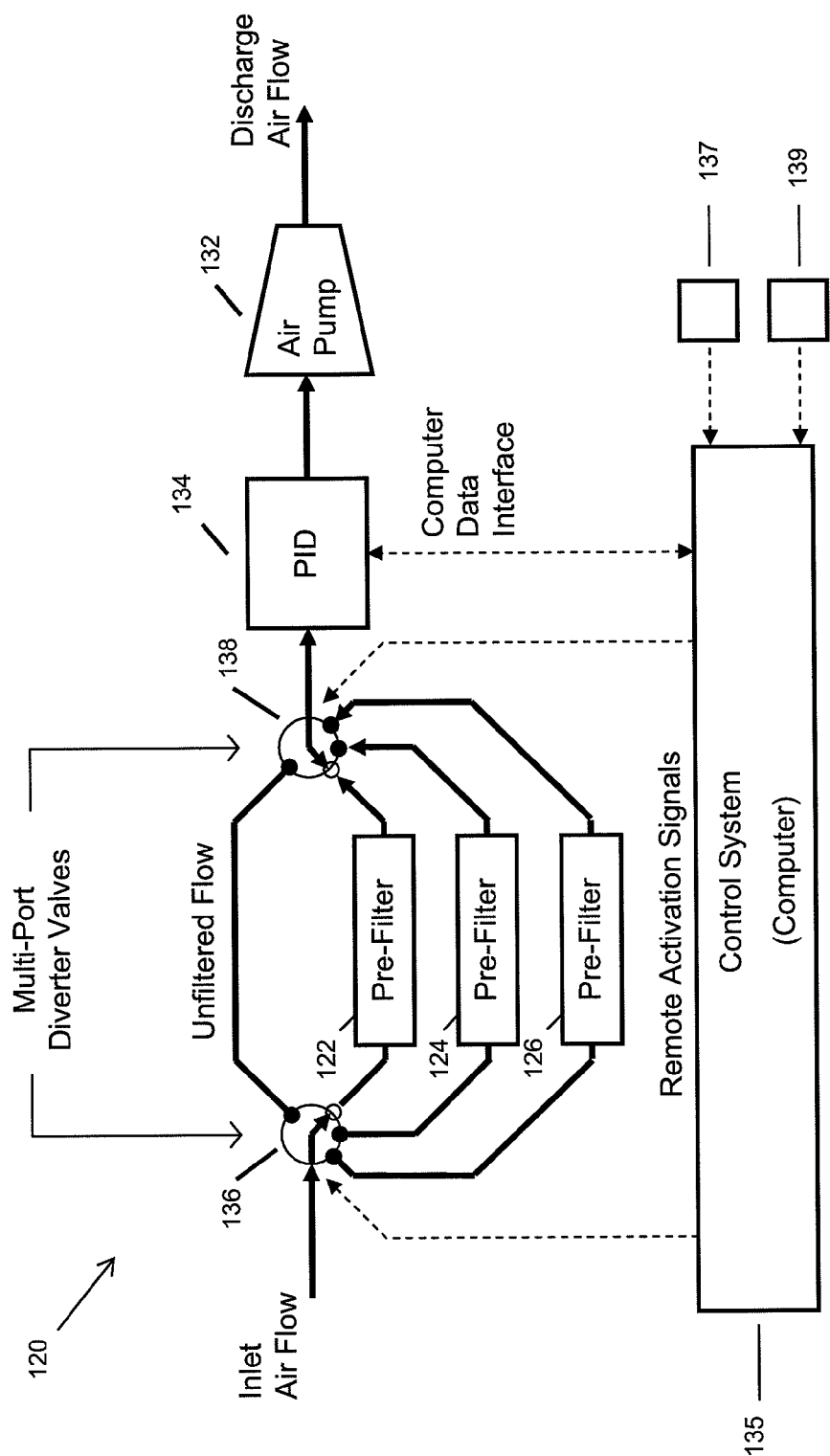
FIG. 5 illustrates a system having a plurality of pre-filters and a diverter valve in accordance with another aspect of the present invention.

In accordance with another aspect of the present invention, a measurement system 120 could be configured with two or more multiple pre-filters. FIG. 5 illustrates the system 120 having three pre-filters 122, 124 and 126. These multiple pre-filters 122, 124 and 126 are arranged in such a manner that the valves 128 and 130 could select a specific filter on a given occasion. This would enable multiple occurrences of filtered VOC measurement before the need to replace expended filters. The valves are capable of isolating all but one flow path from the optional air pump 132 to the PID 134.

In this configuration, the pre-filters 122, 124 and 126 can be all the same type of pre-filter. In this case, the interval for performing maintenance on the system 120 is reduced because the pre-filters 122, 124 and 126 can be switched in and out of the flow path from the air pump to the PID 134 as needed. In accordance with a further aspect of the present invention, a measurement could be taken with pre-filter 122 selected in the air flow path and then another measurement could be taken with pre-filter 124 selected in the air flow path, with the other pre-filters isolated. This will allow the measurement taken with the pre-filter 122 to be checked. If desired, another measurement could be taken with the pre-filter 126 in the air flow path as another check. If a discrepancy is detected between any of the measurements, then an alert can be give that maintenance is needed. The air flow in this system is governed by manifolds 136 and 138, which are controlled so that only one of the air flow paths is active at a time and so that the air flow paths with a filter 122, 124 or 126 are only activated when use of one of the filters 122, 124 or 126 is desired.

This system could be enhanced by operating it in conjunction with a second, unfiltered PID, similar to the system shown in FIG. 4. In this case, a second PID with its own air pump could be operated in parallel with the PID 134, similarly to the embodiment disclosed in FIG. 4. Sensors 137 and alarms 139 provide the control system 135 with start and stop control signals for the diverter valves 136 and 138 and for the PID 134.

Figure 6:
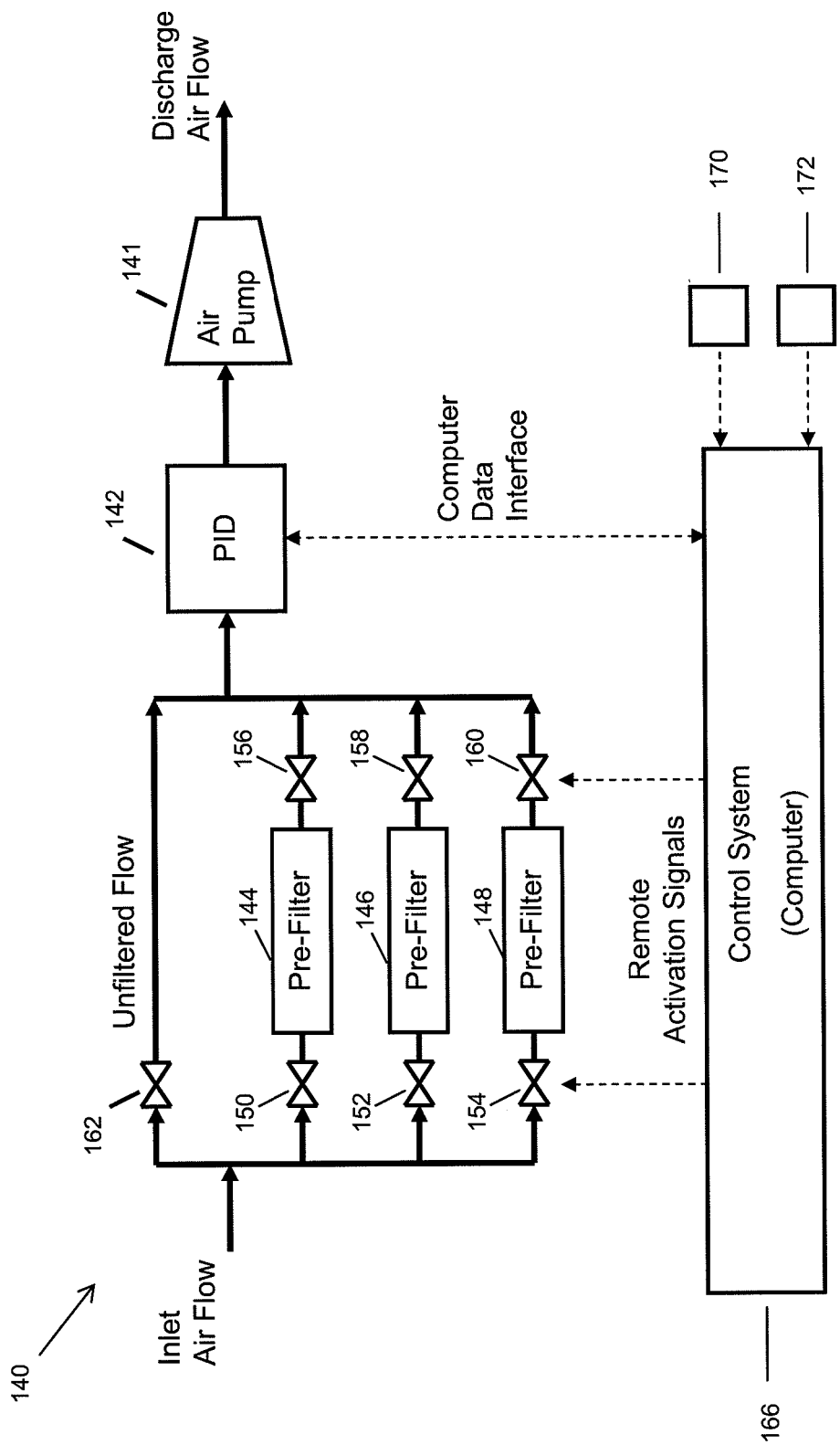
FIG. 6 illustrates a system having a plurality of pre-filters and associated block valves in accordance with an aspect of the present invention.

In accordance with another aspect of the present invention, FIG. 6 illustrates a system 140 having an air pump 141, a PID 142 and multiple pre-filters 144, 146 and 148. Each of the pre-filters 144, 146 and 148 is controlled with a block valve 150, 152 and 154, respectively. Similarly, the outlet of each of the pre-filters 144, 146 and 148 is also controlled with a block valve 156, 158 and 160, respectively. A direct channel of air flow from the air pump 141 and the PID 142 is also controlled with block valve 162.

This system operates similarly to the system of FIG. 5. Only one flow path is enabled at one time so that only one pair of block valves 150 and 156, 152 and 158, 154 and 160, or the single block valve 162 is open to air flow at a time. The control of the block valves is preferably accomplished through control signals issued by a computer 166. Sensors 170 and alarms 172 provide input to the computer 166 through which the computer 166 generates the control signals.

This system could be enhanced by operating it in conjunction with a second, unfiltered PID, similar to the system shown in FIG. 4.

A system of the configuration shown in FIG. 4 could be combined with additional environmental and/or process measurements and a computer software application to predict the remaining service life of a pre-filter. Such additional measurements would be taken in the vicinity of the pre-filter in question. Such additional measurements might include, but would not be limited to, total VOC concentration, ambient temperature, ambient humidity, flow rate through the pre-filter, duration the pre-filter has been in operation exposed to ambient airflow, etc. These measurements would be taken in real-time and at sufficient frequency to allow continuous modeling of the ambient conditions of operation of the pre-filter. This, in turn, would enable the implementation of software calculations to estimate the remaining service life of the pre-filter, for example, but not limited to, estimating the cumulative mass flow of VOCs passing through the pre-filter A system of the configuration shown in FIG. 5 or FIG. 6, having multiple pre-filters available for measurement usage, could be equipped with more than one type of pre-filter installed and ready for service. This would enable switching from one type of pre-filter to another so as to measure the specific concentration of more than one type of VOC, for example benzene and butadiene. Such switching could be done in quick succession, so as to monitor two or more distinct compounds known or suspected to be present at a given time; or it could be done independently, for example based on separate and independent triggering events or alarms.

In accordance with another aspect of this invention, the PID in FIGS. 1-6 can be replaced with any type of VOC detector. Thus, in accordance with one aspect of the present invention, a flame ionization detector (FID) can be used in place of the PID in each of FIGS. 1-6. In accordance with another aspect of the present invention, an electrochemical detector (ECD) can be used in place of the PID in each of FIGS. 1-6. In accordance with another aspect of the present invention, a spectrophotometer can be used in place of the PID in each of FIGS. 1-6.

The present invention has applicability in various scenarios. One scenario is the measurement of benzene concentration in real time. This could be valuable in several industrial settings. For example, in hazardous waste remediation sites where VOCs are present in soil being excavated, monitoring for potential release of benzene into the air is important to successfully performing perimeter monitoring duties for the protection of the public beyond the hazardous waste site. A commonly occurring situation are clean ups of manufactured gas plant (MGP) sites, which have coal tar residue in the soil. Monitoring for benzene at perimeter of petroleum refineries can also be important because these sites can release small quantities of VOCs, including benzene in their chemical process operations. A similar problem can exist at gasoline distribution facilities including bulk terminals and retail service stations. Alternatively, the invention could be used for work zone monitoring to measure or estimate the exposure of workers to substances of interest. Of course, the present invention can be used to determine concentrations of VOCs other than benzene.

Various sensor arrangements can be used to control the valves of the present invention through a computerized control system. For example, an unfiltered detector (such as a PID) could be monitored against a threshold of 5 parts per million (ppm) for total VOCs. If that threshold is reached, a pre-filtered PID could be triggered to monitor for benzene over a period of 15 minutes, taking real-time measurements at a frequency of typically once every 5 seconds. Other frequencies of measurements can be used. These measurements would be used to calculate the average benzene concentration over the 15-minute interval. This average value could then be used to directly compare to a Short Term Exposure Limit (STEL) over the 15-minute interval, or to extrapolate a value to compare to a Permissible Exposure Limits (PEL) applicable to an 8-hour work shift. Acceptable values for STELs and PELs are defined by various regulations specific to environmental applications and settings. For example the Occupational Safety and Health Administration (OSHA) standards for benzene exposure for workers are: 5 ppm STEL for 15-minutes, and 1 ppm PEL for 8-hours.

In accordance with another aspect of this invention, the PIDs and the computer control system of FIG. 4 can be used to estimate the useful service life of the pre-filter. A computer application can be configured to measure various environmental parameters of interest, for example: flow rate through the continuously-unfiltered PID, total VOC concentration through the continuously-unfiltered PID, VOC concentration through the pre-filtered PID, cumulative duration of usage of the pre-filtered PID, and ambient temperature and humidity of the air in the immediate vicinity of the PIDs. This computer application can be configured with an algorithm to use these measured parameters to calculate the mass flow of air through the pre-filter and thus estimate the amount of interfering VOCs trapped by the pre-filter. This calculation can then be compared to the mass flow threshold for breakthrough (failure) of the pre-filter when subjected to the interfering VOCs. This comparison can be used to send an alarm or other notification via the computer system regarding the status of pre-filter with regard to its remaining useful service life.

I claim:

1. A system for monitoring an environment, comprising:
   a first valve having an inlet that is adapted to receive air from the environment and a first and second outlet;
   a second valve having a first and second inlet and an outlet, the first inlet being connected to the first outlet of the first valve;
   a pre-filter connected between the second outlet of the first valve and the first inlet of the second valve, the pre-filter selectively removing one or more compounds from the environment;
   a detector having an inlet connected to the outlet of the second valve, the detector determining a concentration of one or more volatile organic compounds in real-time;
   wherein the first valve and the second valve are configured to either allow air flow from the first outlet of the first valve through the second valve to the detector or from the second outlet of the first valve through the pre-filter to the first inlet of the second valve to the detector.

2. The system of claim 1, wherein the detector is a photo ionization detector.

3. The system of claim 1, wherein the detector is a flame ionization detector.

4. The system of claim 1, wherein the detector is selected from the group consisting of a photo ionization detector, a flame ionization detector, a spectrophotometer and an electrochemical detector.

5. The system of claim 1, further comprising a computerized monitoring system that transmits one or more control signals to the first valve and the second valve to control positions of the first valve and the second valve.

6. The system of claim 5, further comprising a sensor connected to the computerized monitoring system wherein a status of the sensor determines the one or more control signals.

7. The system of claim 1, comprising an air pump connected to the inlet of the first valve or to the outlet of the detector.

8. The system of claim 1, comprising a second pre-filter having an inlet connected to a third outlet of the first valve and an outlet connected to a third inlet of the second valve, wherein the first valve and the second valve are configured to either allow air flow from the first outlet of the first valve through the second valve to the detector or from the second outlet of the first valve through the pre-filter to the first inlet of the second valve to the detector or from the third outlet of the first valve through the second pre-filter to the third inlet of the second valve to the detector.

9. The system of claim 8, further comprising a third pre-filter having an inlet connected to a fourth outlet of the first valve and an outlet connected to a fourth inlet of the second valve, wherein the first valve and the second valve are configured to either allow air flow from the first outlet of the first valve through the second valve to the detector or from the second outlet of the first valve through the pre-filter to the first inlet of the second valve to the detector or from the third outlet of the first valve through the second pre-filter to the third inlet of the second valve to the detector or from the fourth outlet of the first valve through the third pre-filter to the fourth inlet of the second valve to the detector.

* * * * *